United States Patent

Haas

[11] Patent Number: 5,976,140
[45] Date of Patent: Nov. 2, 1999

[54] FOIL FOR BONE GROWTH PROMOTION

[75] Inventor: Franz Haas, Vienna, Austria

[73] Assignee: MKE Metall- und Kunststoffwaren Erzeugungs GmbH, Heidenreichstein, Austria

[21] Appl. No.: 08/865,240

[22] Filed: May 29, 1997

[30] Foreign Application Priority Data

May 29, 1996 [AT] Austria ........................................ 933/96

[51] Int. Cl.$^6$ ................................................ A61B 17/56
[52] U.S. Cl. ................................ 606/69; 606/72; 606/76; 433/173
[58] Field of Search .................................. 606/76, 74, 86, 606/72, 60, 53, 69; 433/173, 174

[56] References Cited

U.S. PATENT DOCUMENTS

| 4,636,215 | 1/1987 | Schwartz | 623/16 |
| 5,196,016 | 3/1993 | Buser et al. | 606/72 |
| 5,443,483 | 8/1995 | Kirsch | 606/74 |
| 5,564,926 | 10/1996 | Branemark | 433/174 |
| 5,824,088 | 10/1998 | Kirsch | 623/16 |

FOREIGN PATENT DOCUMENTS

| 0 622 052 | 11/1994 | European Pat. Off. . |
| 43 02 709 | 7/1994 | Germany . |

Primary Examiner—Guy V. Tucker
Attorney, Agent, or Firm—Herbert Dubno

[57] ABSTRACT

A foil or membrane for covering bone defect locations and for promoting bone regeneration, comprised of titanium and which is inelastic, stress-free and plastically deformable. The foil has a thickness of less than 0.1 mm. The thickness lies especially in a range of 0.025 mm. It is advantageously roughened at least on one surface or grooved. Cut pieces have a cut burr which projects from one surface and in the use of the foil, turned to the bone with sealing edges. A method of making such a foil with the aforesaid characteristics comprises a removal of the surfaces of the rolled foil by a chemical foil until the desired thickness is reached. A nail for fixing the foil in position has a spherical shaped head and in its concavity merges with a saw-tooth barbed pin with a radius.

9 Claims, 2 Drawing Sheets

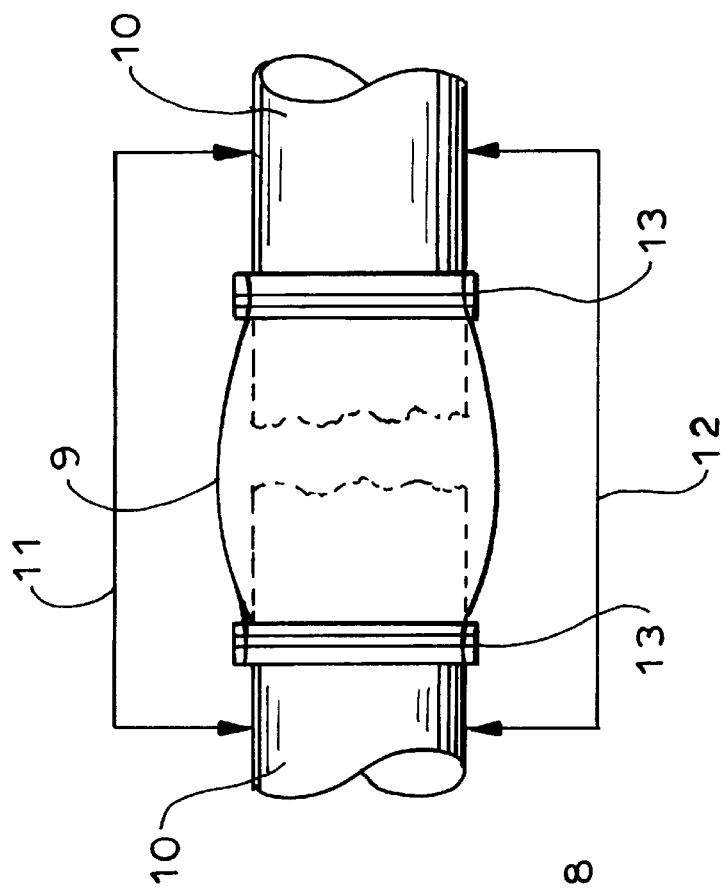
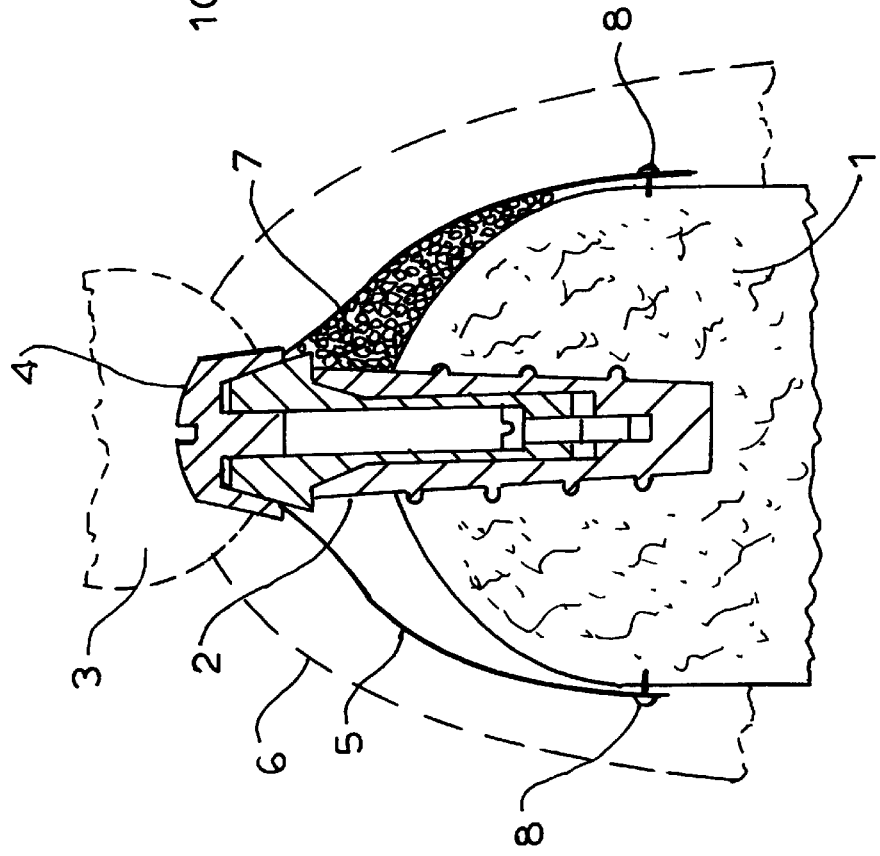

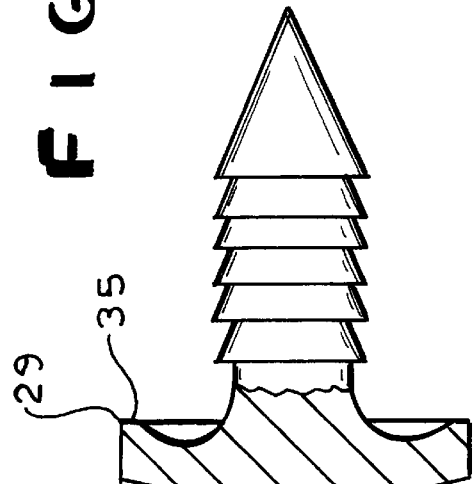
FIG. 3
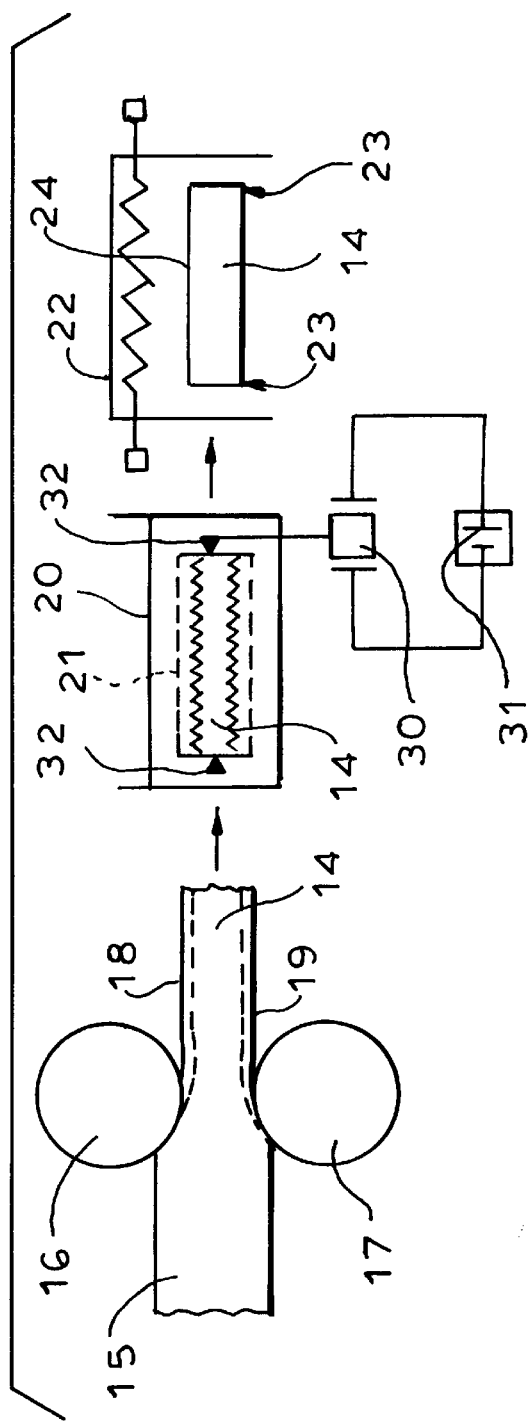
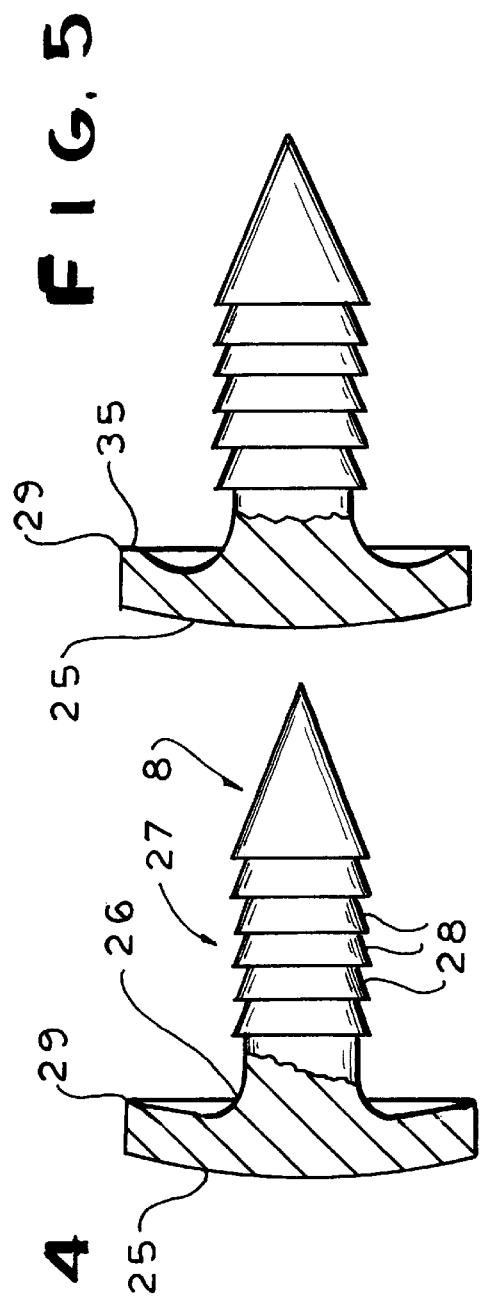
FIG. 4    FIG. 5

FOIL FOR BONE GROWTH PROMOTION

FIELD OF THE INVENTION

My present invention relates to a foil or membrane which can be used to protect a location at which bone growth is to be promoted, to a method of promoting bone growth using such a foil, to a method of making the foil and to a nail for fixing the foil in position. More particularly the invention relates to a foil or membrane for covering a bone defect location such as a defect fracture, alveoli or the like in order to promote bone regeneration.

BACKGROUND OF THE INVENTION

In order to promote the development of bone substances at bone defects, it is known to cover the defect location with a foil so as to hold the soft tissue with the foil from growing into the defect location. It is further known to fill the region in which new bone growth is to occur with a granulate and to cover the volume thereof with a foil. The granulate, usually hydroxyapatite, has a "place holding" function in which the bone growth can occur and the foil is usually composed of a textile material of such fibers as have been long used for the stitching of wounds. This fabric has a protective effect when positioned over the bone defect and held in place by stitching, for example.

The fiber structure at the edges of the fabric, as a result of cutting operations, for example, during a surgical procedure, and the mechanical properties of the textile material, especially its elasticity, are not fully ideal for many applications.

In EP 622 052 A1, a process for forming a foil is described to promote bone growth in the dental field. An image of the defect location is taken, usually digitally, and a model is formed, whereby a stiff foil can be shaped to the model, i.e. given the desired shape. The foil material used was, for example, shape-stable titanium in a thickness of say 0.3 mm.

German patent 43 02 709 C1 deals with a covering of a bone growth region provided with a bone-growth promoter like hydroxyapatite granules, in which the membrane is bendable and ductile and requires a stiffening in the form of a rigid titanium foil of a thickness of 0.3 to 1 mm with perforations.

Titanium metal is also used for dental impressions, bone nails, plates and rails for surgical purposes. The tolerance to titanium is high and X-rays are not obscured because the wall thicknesses of the titanium articles utilized need not be particularly great.

OBJECTS OF THE INVENTION

It is the principal object of the present invention to provide an improved foil or membrane for covering bone defects such as defect fractures or alveoli for promoting bone growth for regeneration, which is free from the drawbacks of earlier systems.

Another object of this invention is to provide an improved foil or membrane which can easily be put in place, which can protect the bone growth region from penetration of soft tissue into the region, which can facilitate the growth of soft tissue over the membrane and which will not induce an adverse reaction if left in place within the organism.

Still another object is to provide a foil or membrane which will not significantly obscure X-ray images taken of structures beneath the foil or membrane.

It is also an object of the invention to provide a method of making the improved membrane, a nail for anchoring that membrane and a method of promoting bone growth utilizing such a membrane.

SUMMARY OF THE INVENTION

These objects and others which will become apparent hereinafter are attained, in accordance with the invention with a membrane for covering a bone defect in the form of an inelastic, stress-free plastically deformable titanium foil having a thickness of less than 0.1 mm and at least one roughened surface.

The invention provides a foil or membrane for covering a bone defect location in an improved manner, especially for use in small regions as for example in jaw surgery, the foil has a thickness of less than 0.1 mm, especially less than 0.025 mm and at least one roughened or grooved surface. Titanium foil is satisfactory for this purpose and has no resiliency which could complicate positioning on the bone. The roughened or grooved surface can be used as an outer side, i.e. the side turned away from the bone and turned toward the soft tissue. The soft tissue holds well to the foil under these conditions. The incorporation of the foil in the gum region of the mouth is thereby facilitated. The roughening can be effected by sandblasting or embossing and the grooving can be effected by electro-erosion or by a laser treatment or even by a chemical surface treatment. An especially advantageous embodiment provides that the foil is cut into pieces of, for example, 3×4 cm and that during the cutting operation, a burr is formed all around the perimeter which projects above one of the foil surfaces. The burr is thus directional in character and can form a projecting sealing edge which can engage the bone so as to prevent the growth of soft tissue beneath the foil. A bandage, e.g. of suturing material can be applied to the places at which the foil is applied to the bone to ensure a sealed joint.

A titanium foil can be rolled to a thickness in the range of that desired for the foil. The rolling process tends to compact the surface structure and to the extent that it imparts a resilient characteristic which might affect detrimentally the ability to fit the foil to the bone, this is undesirable. Rather it is preferred to provide a stress-free and plastically-deformable foil.

To form a stress-free and plastically-deformable titanium foil it can be subjected to a thermal treatment. It is, however, a preferred embodiment of the invention to roll the foil to a thickness greater than the desired wall thickness of the foil and then subject the rolled sheet of a chemical treatment, i.e. a chemical etching, preferably with hydrofluoric acid to eliminate the stressed surface regions, and to reduce the thickness of the etched sheet to the desired foil thickness. The chemical treatment removes the boundary layers of the titanium sheet, i.e. those layers which may retain a resiliency. Upon reaching the desired foil thickness of about 0.1 mm or less, the etched foil is washed and dried, for example, in a drying furnace at about 100° C. Possible residual stress is thereby completely neutralized.

The stress-free titanium foil can easily and irreversibly be brought to the desired shape and for retaining the foil in its surgical application, titanium nails can be used. The titanium nails are preferably provided with ball-shaped heads with a spherical outer surface and a spherically concave inner surface surrounded by a circular abutment edge or annular surface which bears against the foil. The transition between the ball-shaped concave inner surface and the barbed shank of the nail is formed by rounding or radius. The shank itself can have a sawtooth cross sectional contour formed by adjoining frustoconical surfaces.

The circular rim of the nail head thus sealingly engages the titanium foil upon being driven into the bone while the shank can force a hole in the foil. The shank presses the foil material outwardly so that it can bulge into the concavity of the head. The best matching of the nail to the foil is accomplished with the radius in the transition between the spherically concave surface of the head and the shank. The shank itself has a number of barbs formed by the adjoining frustoconical surfaces.

A method of promoting bone regeneration according to the invention comprises the steps of:

(a) fitting a membrane for covering a bone defect to facilitate bone regeneration over the bone defect, the membrane comprising an inelastic, stress-free plastically deformable titanium foil having a thickness of less than 0.1 mm and at least one roughened surface; and (b) securing the membrane over the bone defect with at least one nail holding the foil against the bone, the nail having a head and a barbed shank extending from the head, the head having a spherically curved outwardly convex surface turned away from the shank, an spherically concave side turned toward the shank, a radius joining the spherically concave side with the shank, and an outer circular annular rim on a side of the head turned toward the shank for retaining the foil against the bone.

BRIEF DESCRIPTION OF THE DRAWING

The above and other objects, features, and advantages will become more readily apparent from the following description, reference being made to the accompanying drawing in which:

FIG. 1 is a diagrammatic section through a jaw bone in the region of an implant illustrating the use of the foils of the invention to induce bone growth around the implant;

FIG. 2 is a diagrammatic cross section showing use of a foil in accordance with the invention for the repair of a defect fracture;

FIG. 3 is a diagram illustrating steps in the production of the foil of the invention;

FIG. 4 is an elevational view partly broken away showing a nail for fastening the foil to the bone; and FIG. 5 is a view similar to FIG. 4 of another nail.

SPECIFIC DESCRIPTION

FIG. 1 shows a jaw bone 1 into which a primary part 2 of an implant has been set in the usual manner by drilling a hole in the jaw bone and screwing this anchor portion of the implant into it. The upper opening of the jaw bone is closed with a screw cap 4 which can be removed to allow a tooth to be secured to the primary part as a secondary part of the implant. To raise the level of the bone substance around the implant, i.e. to grow bone substance on the raw bone 1 around the implant substantially to the region at which the tooth 3 is to be joined thereto, a plastically deformable inelastic stress-free titanium foil 5 of a thickness of less than 0.1 mm and preferably less than 0.025 mm, say about 0.020 mm, is clamped between the screw cap 4 and the anchor portion 2 of the implant and forms an apron around the region to be filled with bone. The titanium foil is anchored by bone nails 8 to the jaw bone 1. Soft tissue, namely gum tissue, can grow over the roughened surface of the titanium foil, which is turned outwardly, and the titanium foil prevents the soft tissue 6 from growing into the bone region in which bone growth is desired.

The space between the foil 5 and the jaw bone 1 can be filled with hydroxyapatite granules 7 as a place holder for the bone growth. The hydroxyapatite promotes rapid bone growth and is incorporated in the bone substance as it is formed. Since the hollow space in which the bone growth occurs is protected by the foil, the bone growth is particularly rapid.

A tight seal of the foil is desired both at the anchor portion 2 of the implant and to the jaw bone. For that purpose, the foil 5 can have a small central hole through which the shaft of the screw cap 4 can pass. The screw cap 4 is provided with a conical shape and can sit on the cone of the implant. The foil 5 is then clamped between the cap cone and the implant cone.

The nails 8 can have the configuration shown in FIG. 4.

The titanium foil allows plastic shaping of the foil to the bone 1 and by fold formation, it is possible to impart to the foil the configuration of the bone in the growth region. The titanium foil is completely inelastic so that there is no restoring force developed during its shaping to the bone 1 and the implant 2.

As noted, the outer surface of the foil 5 has been roughened so that the soft tissue 6 adheres firmly thereto. The requisite degree of roughness can be provided by sand blasting, embossing, chemical surface treatment or laser treatment, e.g. by grooving. The foil 5 of titanium can remain in position and need not be removed. X-ray images are hardly affected by it so that changes in the region of the implant can be followed by X-ray imaging even below the foil 5.

In FIG. 2 the use of an equivalent foil 9 in conjunction with a defect fracture of a bone 10 has been shown. The bone 10 or the fracture is secured in place by plates, nails or frames symbolized by the brackets represented at 11 and 12. The fracture region, in which bone material is absent, can be enclosed in a sleeve-like manner by the inelastic, stress-free plastically deformable foil 9 of titanium and anchored to the bone by bandages 13 which also seal the foil to the bone. The foil 9 holds the soft tissue in the region of the break away from the fracture so that the growth of bone between the two parts of the fracture can be accomplished rapidly. In such cases, one can reckon with a bone substance growth of 1 mm in 10 days.

FIG. 3 shows a process for producing a foil 14 of titanium sheet. The titanium sheet 15 is subjected to at least one rolling process via rolls 16, 17 whereby the titanium sheet is rolled to a thickness of about 2.25 mm. The surface regions 18 and 19 of the rolled sheet for a compacted structure which appears to impart a certain round of resiliency to the rolled sheet.

In a subsequent chemical etching treatment in a bath 20, e.g. an acid bath, the surface regions 18 and 19 are etched away on both sides of the foil piece 21, the use of hydrofluoric acid has been found to be especially advantageous for this purpose.

With the etching in the chemical bath, the desired foil thickness of, for example, 0.015 to 0.20 mm can be obtained simultaneously with elimination of stress and the development of an inelastic plastically deformable property. It is not the purpose of the etching to make the foil as thin as possible. Rather it is the purpose of the etching to eliminate resilience, and stress while rendering the foil plastically deformable at the maximum strength of the foil.

In FIG. 5 I have shown another nail wherein at the rim 29 of the head 25, a surface 35 is provided to engage the foil as opposed to the sharp edge at the rim 29 in FIG. 4.

EXAMPLE 1

A titanium foil is rolled to a foil thickness of 0.2 mm and is etched in a hydrofluoric acid bath to a foil thickness of 0.1 mm. Approximately 0.05 mm is removed from each of the wide surfaces of the foil. As a consequence, the foil at this thickness of 0.1 mm is inelastic, stress-free and plastically deformable.

EXAMPLE 2

By increasing the residence time of the foil in the hydrofluoric acid bath, a rolled titanium sheet of an original thickness of 0.203 mm can be brought to a thickness of 008 mm. This produces simultaneously a roughening depth of about 0.005 to about 0.007 mm which is most suitable for the growth of tissue thereon.

EXAMPLE 3

A rolled foil of a thickness of 0.2 mm is etched in a hydrofluoric acid bath and in the latter a standing wave in the ultrasonic range is generated with a quartz oscillator. Resonance is detected in the electrical part of the oscillation circuit. The standing wave tends to generate structure on the surfaces of the titanium foil in the form of uniform grooving because of differential etching in the hydrofluoric acid bath. The final foil thickness was 0.08 to 0.035 mm.

EXAMPLE 4

By a hydrofluoric acid treatment, a titanium foil of 0.08 mm thickness is reduced to 0.02 mm. Such foil thicknesses are particularly suitable for dental purposes because they allow particularly good penetration for X-rays.

In FIG. 3 a quartz oscillator 30 has been shown connected to a circuit 31 supplying the quartz oscillator with electrical energy. The frequency applied to the foil can be adjustable. The frequency is so selected that the foil 14 is subjected between its mounts 32 to a standing wave giving rise to the desired surface structure in the hydrofluoric acid bath.

The foil 14 can be cut into rectangular foil pieces 21 which can be perforated on a small side and which can be hung as strips in the chemical bath. The suspension allows the ultrasound to be coupled to the foil. After washing of the acid from the titanium strips, drying is carried out in a drying chamber 22 at, for example, 100° C. The thermal conditioning can eliminate any residual stresses.

Ahead of the heating treatment, the surface of the foil can be sandblasted or grooved by laser and cut into a commercial size (e.g. 3×4 cm) with the cutting being so carried out that a burr 23 is formed all around the perimeter of the foil. This burr 23 can project opposite the roughened surface 24 and can serve as a sealing lip. Other treatment processes, for example, annealing with subsequent cooling, can be used with good results as well although not as optimally as the treatment described.

To fix the foil covering on bone defects, for example, on defect fractures, alveoli or the like, the foil which is shaped in the manner described, is secured by nails 8 of titanium and with the configuration of FIG. 4. The nails have a ball-shaped head 25 whose convex side is turned away from the shank 27 while the shank extends from the concave side of the head to a point and is formed between the point and the head with a row of frustoconical barbs 28.

The head has a circular rim 29 which can form a sealing edge against the foil 5. The concave portion on the underside of the head serves to receive wrinkled portions of the foil which may gather between the pin 27 and the bone. This concavity, therefore, collects material of the foil and bone material which may be displaced as the nail is driven into the bone through a hole in the foil 5 formed by piercing by the shank.

I claim:

1. A membrane assembly for covering a bone defect to facilitate bone regeneration, comprising an inelastic, stress-free plasmically deformable titanium foil having a thickness of less than 0.1 mm and at least one chemically etched roughened surface, and at least one bone nail pierced through said foil and securing said foil to a bone, said foil being cut into a piece with dimensions of about 3×4 cm and being formed with a burr projecting above one of the surfaces of the foil around an entire perimeter thereof.

2. The membrane assembly defined in claim 1 wherein said foil is of a thickness of less than 0.025 mm.

3. The membrane assembly defined in claim 1 wherein said surface is grooved.

4. The membrane assembly defined in claim 1 wherein said foil has both of its broad surfaces roughened.

5. The membrane assembly defined in claim 4 wherein said surfaces are grooved.

6. A membrane assembly for covering a bone defect to facilitate bone regeneration, comprising an inelastic, stress-free plasmically deformable titanium foil having a thickness of less than 0.1 mm and at least one chemically etched roughened surface, and at least one bone nail pierced through said foil and securing said foil to a bone, said nail having a head and a barbed shank extending from said head, said head having a spherically curved outwardly convex surface turned away from said shank, a spherically concave side turned toward said shank, a radius joining said spherically concave side with said shank, and an outer circular annular rim on a side of said head turned toward said shank for retaining the foil against said bone.

7. The assembly defined in claim 6 wherein said rim is a circular edge.

8. The assembly defined in claim 6 wherein said rim is a circular surface.

9. A method of promoting bone regeneration of bone defects including defect fractures and alveoli, comprising the steps of:

(a) fitting a membrane for covering a bone defect to facilitate bone regeneration over said bone defect, said membrane comprising an inelastic, stress-free plastically deformable titanium foil having a thickness of less than 0.1 mm and at least one chemically etched roughened surface; and (b) securing said membrane over said bone defect with at least one nail holding said foil against the bone, said nail having a head and a barbed shank extending from said head, said head having a spherically curved outwardly convex surface turned away from said shank, an spherically concave side turned toward said shank, a radius joining said spherically concave side with said shank, and an outer circular annular rim on a side of said head turned toward said shank for retaining the foil against the bone.

* * * * *